United States Patent
La Vay et al.

(10) Patent No.: US 7,670,594 B1
(45) Date of Patent: Mar. 2, 2010

(54) HAIR AND SKIN CONDITIONING COMPOSITIONS

(75) Inventors: Carter La Vay, Riverside, CT (US); Anthony J. O'Lenick, Jr., Dacula, GA (US)

(73) Assignee: Zenetech LLC, Old Greenwich, CT (US)

( * ) Notice: Subject to any disclaimer, the term of this patent is extended or adjusted under 35 U.S.C. 154(b) by 1659 days.

(21) Appl. No.: 10/867,999

(22) Filed: Jun. 16, 2004

Related U.S. Application Data

(63) Continuation-in-part of application No. 10/118,009, filed on Apr. 9, 2002, now abandoned.

(51) Int. Cl.
*A61Q 5/00* (2006.01)
(52) U.S. Cl. .................................. 424/70.1
(58) Field of Classification Search ............ 424/70.1
See application file for complete search history.

(56) References Cited

U.S. PATENT DOCUMENTS

| | | | | |
|---|---|---|---|---|
| 4,698,178 | A | * | 10/1987 | Huttinger et al. ............... 516/23 |
| 4,724,851 | A | * | 2/1988 | Cornwall et al. ............ 132/203 |
| 5,226,923 | A | * | 7/1993 | O'Lenick, Jr. ............... 8/115.6 |
| 5,412,074 | A | * | 5/1995 | Jones et al. ................. 530/353 |
| 5,415,860 | A | * | 5/1995 | Beucherie et al. ........... 424/401 |
| 5,589,177 | A | * | 12/1996 | Herb et al. .................. 424/401 |
| 5,733,536 | A | * | 3/1998 | Hill et al. ................. 424/70.12 |
| 5,804,099 | A | * | 9/1998 | Heilen et al. ................. 516/124 |
| 5,866,041 | A | * | 2/1999 | Svarz et al. .................... 516/11 |
| 6,030,628 | A | * | 2/2000 | Schneider et al. ........... 424/401 |

* cited by examiner

*Primary Examiner*—Blessing M Fubara

(57) ABSTRACT

The present invention relates to a series of compositions that are very effective hair and skin conditioners. These compositions are composed of a poloxomer ester and an alkyl dimethicone copolyol. The poloxomer ester has from 14 to 40 carbon atoms in the alkyl group, at least one polyoxypropylene group and between and at least 40% by weight polyoxyethylene group in the molecule. The inclusion of the alkyl group in the alkyl dimethicone copolyol improves wet comb and skin feel.

20 Claims, No Drawings

HAIR AND SKIN CONDITIONING COMPOSITIONS

RELATED APPLICATION

This application is a continuation in part of application Ser. No. 10/118,009, filed Apr. 9, 2002 now abandoned.

FIELD OF THE INVENTION

The present invention relates to a series of compositions that are very effective hair and skin conditioners. These compositions are composed of a poloxomer ester and an alkyl dimethicone copolyol. The poloxomer ester has from 14 to 40 carbon atoms in the alkyl group, at least one polyoxypropylene group and between and at least 40% by weight polyoxyethylene group in the molecule. The poloxomer ester so configured will be water dispersible. The alkyl dimethicone copolyol will have at least 40% polyoxyethylene in the molecule. The presence of the alkyl group on the dimethicone copolyol unexpectantly significantly improves wet comb on hair and removes stickiness on skin. The compositions when applied to the skin and hair provide a very smooth, cosmetically appealing feeling as well as providing softening, emmoliency and gloss.

BACKGROUND OF THE INVENTION

It has long been the desire of mankind to protect the skin and hair from environmental factors that cause damage to them as well as to provide a treatment for such damage after it occurs. The hair and skin often become dry wrinkled as they are exposed to day-to-day stresses in the environment. These stresses include but are not limited to sun, smoke, ozone and environmental pollution. The hair and skin so exposed may appear dry and cosmetically unappealing.

The possibility of avoiding these environmental conditions and consequently the effects of it on hair and skin is all but impossible in today's world. Consequently, there is a need for products that make hair and skin more cosmetically acceptable in appearance. Over the years, many approaches have been tried, with limited success.

Poloxomer is a term applied to compounds that are made up of both ethylene oxide and propylene oxide in a so-called block polymer. Compounds of this type conform to the following structure:

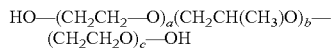

HO—(CH$_2$CH$_2$—O)$_a$(CH$_2$CH(CH$_3$)O)$_b$—(CH$_2$CH$_2$O)$_c$—OH wherein a and c are each independently integers ranging from 0 to 20, with the proviso that a+c be at least 5;

b is an integer ranging from 1 to 20;

with the proviso that a+c be at least 5.

Silicone compounds have been known for a number of years. They however suffer from several inherent problems that minimize their effectiveness in personal care applications. Dimethicone, also called silicone fluids are water insoluble, mineral oil insoluble products that have been applied to the skin. The lack of solubility in many systems, the greasy nature and the cosmetically unacceptable feel on the skin has limited the use of these products in personal care applications.

The incorporation of water-soluble groups onto the silicone backbone has resulted in a series of water-soluble products known as dimethicone copolyol. These materials are easily formulated into water-based systems, but because of their water solubility, remain in the water and provide little in terms of skin and hair treatment.

U.S. Pat. No. 5,226,923 to O'Lenick, entitled Silicone fatty esters as conditioning agents describes certain dimethicone copolyol esters used as conditioners. These materials combine in one molecule a fatty group a silicone group and a water-soluble group. While interesting as emulsifiers, and non-yellowing softeners, this approach does little to address the need for products that provide functional attributes on the hair and skin vis-á-vis conditioning and softening.

Surprisingly, by incorporating a poloxomer ester and a dimethicone copolyol, in separate molecules into a composition, resulting in surprisingly efficacious products, heretofore unattainable.

SUMMARY OF THE INVENTION

The present invention relates to a series of compositions that are very effective hair and skin conditioners. These compositions are composed of a poloxomer ester and a dimethicone copolyol. The poloxomer ester has from 14 to 40 carbon atoms in the alkyl group, at least one polyoxypropylene group and at least 40% by weight polyoxyethylene group in the molecule. The poloxomer ester so configured will be water dispersible. The alkyl dimethicone copolyol will have at least 40% by weight polyoxyethylene in the molecule and at least one alkyl group on the molecule. The alkyl dimethicone copolyol will have at least 40% polyoxyethylene in the molecule. The presence of the alkyl group on the dimethicone copolyol unexpectantly significantly improves wet comb on hair and removes stickiness on skin. The compositions when applied to the skin and hair provide a very smooth, cosmetically appealing feeling as well as providing softening, emmoliency and gloss.

OBJECT OF THE INVENTION

It is one object of the present invention to provide a series of compositions that are highly effective in the softening, conditioning, wet comb properties, skin feel and moisturizing hair and skin when applied out of aqueous systems.

It is another objective of the present invention to provide a process for treating hair and skin, which comprises contacting the hair or skin with an effective conditioning concentration of the compositions of the present invention.

DETAILED DESCRIPTION OF THE INVENTION

We have surprisingly found that the incorporation of polyoxypropylene into the backbone of the ester, and combining the resulting material with alkyl dimethicone copolyol unexpectantly significantly improves wet comb on hair and removes stickiness on skin. The compositions when applied to the skin and hair provide a very smooth, cosmetically appealing feeling as well as providing softening, emmoliency and gloss. We in part attribute the functionality to the fact that the incorporation of the methyl branch in the molecule results in a composition that has improved properties over the products made with on polyoxypropylene groups. Esters prepared using polyoxypropylene groups in the backbone are referred to as poloxomer esters.

We have also learned that the best functional results on hair and skin are obtained using a poloxomer ester that is minimally water-soluble or better yet water dispersible and the dimethicone copolyol is water-soluble. The poloxomer ester should have between 14 and 20 carbon atoms, at least one polyoxypropylene group and at least 40% polyoxyethylene by weight. The dimethicone copolyol should have at least 40% polyoxyethylene groups present, in order to be water-soluble.

The compositions of the present invention are hair and skin conditioning compositions, which comprises;
(a) from between 5% to 95% by weight of a poloxomer ester conforming to the following structure:

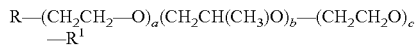

wherein;

R and $R^1$ are selected from the group consisting of H and —C(O)—$R^2$, with the proviso that both R and R1 are not both H;

a and c are each independently integers ranging from 0 to 20, with the proviso that a+c be at least 5;

b is an integer ranging from 1 to 20;

with the proviso that a+c be at least 5;

$R^2$ is selected from the group consisting of;

a is an integer ranging from 0 to 20;

b is an integer ranging from 1 to 20;

c is an integer ranging from 0 to 20;

with the proviso that a+c be at least 5;

$R^2$ is selected from the group consisting of;

$CH_3—(CH_2)_m C(O)—O—$; $CH_3 (CH_2)_5 CH(OH)—(CH_2)_{10}—C(O)O—$;

$CH_3—(CH_2)_7—CH=CH—(CH_2)_7—C(O)O—$; and ricionelic;

m is an integer ranging from 6 to 38.

said poloxomer ester should have at least 40% by weight polyoxyethylene in the backbone;

and (b) between 95% to 5% by weight of a silicone conforming to the following structure;

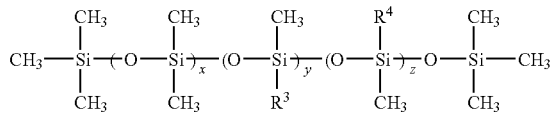

wherein;

$R^3$ is $(CH_2)_3O—(CH_2CH_2—O)_d(CH_2CH(CH_3)O)_e—(CH_2CH_2—O)_f—H$ $R^4$ is alkyl having 10 to 22 carbon atoms;

x is an integer ranging from 0 to 200;

y is an integer ranging from 1 to 45;

z is an integer ranging from 1 to 45;

d is an integer ranging from 0 to 20;

e is an integer ranging from 0 to 20 ;

f is an integer ranging from 0 to 20;

with the proviso that d+f be at least 5;

said silicone should have at least 40% by weight polyoxyethylene in the molecule.

In addition, the invention is drawn to a process of conditioning hair and skin, which comprises contacting the hair and skin with an effective conditioning concentration of a composition, which comprises;

(a) from between 5% to 95% by weight of a poloxomer ester conforming to the following structure:

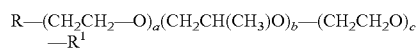

wherein;

R and $R^1$ are selected from the group consisting of H and —C(O)—$R^2$, with the proviso that both R and R1 are not both H;

a and c are each independently integers ranging from 0 to 20, with the proviso that a+c be at least 5;

b is an integer ranging from 1 to 20;

with the proviso that a+c be at least 5;

$R^2$ is selected from the group consisting of;

$CH_3—(CH_2)_m C(O)—O—$; $CH_3 (CH_2)_5 CH(OH)—(CH_2)_{10}—C(O)O—$;

$CH_3—(CH_2)_7—CH=CH—(CH_2)_7—C(O)O—$; and ricionelic;

m is an integer ranging from 6 to 38;

said poloxomer ester should have at least 40% by weight polyoxyethylene in the backbone;

and (c) between 95% to 5% by weight of a silicone conforming to the following structure;

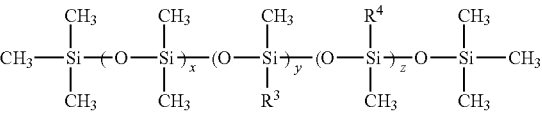

wherein;

$R^3$ is $(CH_2)_3O—(CH_2CH_2—O)_d(CH_2CH(CH_3)O)_e—(CH_2CH_2O)_f—H$ $R^4$ is alkyl having 10 to 22 carbon atoms;

x is an integer ranging from 0 to 200;

y is an integer ranging from 1 to 45;

z is an integer ranging from 1 to 45:

d is an integer ranging from 0 to 20;

e is an integer ranging from 0 to 20;

f is an integer ranging from 0 to 20;

with the proviso that d+f be at least 5;

said silicone should have at least 40% by weight polyoxyethylene in the molecule.

Said effective conditioning concentration ranges from between 0.5% and 60% by weight of the composition in water.

Both the poloxomer ester and the alkyl dimethicone copolyol contain a polyoxyethylene group —$(CH_2CH_2O)$. This group increases water solubility of the molecule. Both molecules also possess a water insoluble group. In the case of the poloxomer ester it is the $R^1$ group. In the case of the dimethicone copolyol, it is the silicone backbone. The poloxomer ester also contains a polyoxypropylene group, which we have found improves the conditioning, softening and emmoliency of the composition.

Poloxomer Ester $$R-(CH_2CH_2-O)_a(CH_2CH(CH_3)O)_b-(CH_2CH_2O)_c-R^1$$

wherein;

R and $R^1$ are selected from the group consisting of H and —C(O)—$R^2$, with the proviso that both R and R1 are not both H;

a and c are the subscripts for the water soluble groups;

b is the subscript for the all-important methyl branched polyoxypropylene group.

Alkyl Dimethicone Copolyol

The alkyl dimethicone copolyol contains water soluble polyoxyethyene groups. They are the groups having d and f as subscripts. The alkyl dimethicone copolyol also has a water insoluble silicone group. This group has x as a subscript.

$$CH_3-Si(CH_3)_2-(O-Si(CH_3)_2)_x-(O-Si(CH_3)(R^3))_y-(O-Si(R^4)(CH_3))_z-O-Si(CH_3)_3$$

wherein;

$R^3$ is $(CH_2)_3O-(CH_2CH_2-O)_d(CH_2CH(CH_3)O)_e-(CH_2CH_2O)_f-H$ $R^4$ is alkyl having 10 to 22 carbon atoms;

x is an integer ranging from 0 to 200;

y is an integer ranging from 1 to 45;

z is an integer ranging from 1 to 45:

d is an integer ranging from 0 to 20;

e is an integer ranging from 0 to 20;

f is an integer ranging from 0 to 20;

with the proviso that d+f be at least 5;

said silicone should have at least 40% by weight polyoxyethylene in the molecule.

The present invention also relates to a process of conditioning hair and skin, which comprises contacting the hair and skin with an effective conditioning concentration of a composition, which comprises;

(a) from between 5% to 95% by weight of a poloxomer ester conforming to the following structure:

$$R-(CH_2CH_2-O)_a(CH_2CH(CH_3)O)_b-(CH_2CH_2O)_c-R^1$$

wherein;

R and $R^1$ are selected from the group consisting of H and —C(O)—$R^2$, with the proviso that both R and $R^1$ are not both H;

a and c are each independently integers ranging from 0 to 20, with the proviso that a+c be at least 5;

b is an integer ranging from 1 to 20; with the proviso that a+c be at least 5;

$R^2$ is selected from the group consisting of;

$CH_3-(CH_2)_m C(O)-O-$; $CH_3 (CH_2)_5 CH(OH)-(CH_2)_{10}-C(O)O-$;

$CH_3-(CH_2)_7-CH=CH-(CH_2)_7-C(O)O-$; and ricionelic;

m is an integer ranging from 6 to 38;

said poloxomer ester should have at least 40% by weight polyoxyethylene in the backbone;

and (d) between 95% to 5% by weight of a silicone conforming to the following structure;

$$CH_3-Si(CH_3)_2-(O-Si(CH_3)_2)_x-(O-Si(CH_3)(R^3))_y-(O-Si(R^4)(CH_3))_z-O-Si(CH_3)_3$$

wherein;

$R^3$ is $(CH_2)_3-O-(CH_2CH_2-O)_d(CH_2CH(CH_3)O)_e-(CH_2CH_2O)_f-H$ $R^4$ is alkyl having 10 to 22 carbon atoms;

x is an integer ranging from 0 to 200;

y is an integer ranging from 1 to 45;

z is an integer ranging from 1 to 45:

d is an integer ranging from 0 to 20;

e is an integer ranging from 0 to 20;

f is an integer ranging from 0 to 20;

with the proviso that d+f be at least 5;

said silicone should have at least 40% by weight polyoxyethylene in the molecule.

said effective conditioning concentration ranges from between 0.5% and 60% by weight of the composition in water.

PREFERRED EMBODIMENTS

In a preferred embodiment $R^1$ is H and R is —C(O)—$R^2$.

In a preferred embodiment both R and $R^1$ are —C(O)—$R^2$.

In a preferred embodiment $R^2$ is $CH_3-(CH_2)_m C(O)-O-$;

In a preferred embodiment $R^2$ is $CH_3 (CH_2)_5 CH(OH)-(CH_2)_{10}-C(O)O-$.

In a preferred embodiment $R^2$ is $CH_3-(CH_2)_7-CH=CH-(CH_2)_7-C(O)O-$.

In a preferred embodiment e is 0.

In a preferred embodiment e is 1 to 5.

In a preferred embodiment x is 0.

In a preferred embodiment $R^4$ is alkyl having 12 carbon atoms.

In a preferred embodiment $R^4$ is alkyl having 16 carbon atoms.

In a preferred embodiment $R^4$ is alkyl having 18 carbon atoms.

EXAMPLES

Alkyl Dimethicone Copolyol

Alkyl dimethicone copolyol compounds are known materials and are available from a variety of commercial sources including Siltech LLC, Dacula, Ga. They conform to the following structure:

$$CH_3-\underset{\underset{CH_3}{|}}{\overset{\overset{CH_3}{|}}{Si}}-(O-\underset{\underset{CH_3}{|}}{\overset{\overset{CH_3}{|}}{Si}})_x-(O-\underset{\underset{R^3}{|}}{\overset{\overset{CH_3}{|}}{Si}})_y-(O-\underset{\underset{CH_3}{|}}{\overset{\overset{R^4}{|}}{Si}})_z-O-\underset{\underset{CH_3}{|}}{\overset{\overset{CH_3}{|}}{Si}}-CH_3$$

wherein;

$R^3$ is $(CH_2)_3-O-(CH_2CH_2-O)_d(CH_2CH(CH_3)O)_e-(CH_2CH_2O)_f-H$ $R^4$ is alkyl having 10 to 22 carbon atoms;

x is an integer ranging from 0 to 200;

y is an integer ranging from 1 to 45;

z is an integer ranging from 1 to 45:

d is an integer ranging from 0 to 20;

e is an integer ranging from 0 to 20;

f is an integer ranging from 0 to 20;

with the proviso that d+f be at least 5;

Poloxomer Esters

Poloxomer compounds are compounds of commerce and are available from a variety of sources including Siltech LLC Dacula, Ga.

$$R-(CH_2CH_2-O)_a(CH_2CH(CH_3)O)_b-(CH_2CH_2O)_c-R^1$$

wherein;

R and $R^1$ are selected from the group consisting of H and $-C(O)-R^2$, with the proviso that both R and $R^1$ are not both H;

a and c are each independently integers ranging from 0 to 20, with the proviso that a+c be at least 5;

b is an integer ranging from 1 to 20;

with the proviso that a+c be at least 5;

$R^2$ is selected from the group consisting of;

$CH_3-(CH_2)_mC(O)-O-$; $CH_3\ (CH_2)_5CH(OH)-(CH_2)_{10}-C(O)O-$;

$CH_3-(CH_2)_7-CH=CH-(CH_2)_7-C(O)O-$; and ricionelic;

m is an integer ranging from 6 to 38;

Examples

| Example | R | $R^1$ | a | b | c | $R^2$ | m |
|---|---|---|---|---|---|---|---|
| 11 | $-C(O)-R^2$ | H | 0 | 1 | 5 | $CH_3-(CH_2)_mC(O)-O-$ | 6 |
| 12 | $-C(O)-R^2$ | H | 20 | 20 | 20 | $CH_3-(CH_2)_mC(O)-O-$ | 8 |
| 13 | $-C(O)-R^2$ | H | 10 | 1 | 0 | $CH_3-(CH_2)_mC(O)-O-$ | 10 |
| 14 | $-C(O)-R^2$ | H | 10 | 5 | 10 | $CH_3-(CH_2)_mC(O)-O-$ | 16 |
| 15 | $-C(O)-R^2$ | H | 5 | 5 | 5 | $CH_3-(CH_2)_mC(O)-O-$ | 18 |
| 16 | $-C(O)-R^2$ | H | 5 | 10 | 10 | $CH_3-(CH_2)_mC(O)-O-$ | 38 |
| 17 | $-C(O)-R^2$ | $-C(O)-R^2$ | 0 | 1 | 5 | $CH_3-(CH_2)_mC(O)-O-$ | 6 |
| 18 | $-C(O)-R^2$ | $-C(O)-R^2$ | 20 | 20 | 20 | $CH_3-(CH_2)_mC(O)-O-$ | 8 |
| 19 | $-C(O)-R^2$ | $-C(O)-R^2$ | 10 | 5 | 0 | $CH_3-(CH_2)_mC(O)-O-$ | 16 |
| 20 | $-C(O)-R^2$ | $-C(O)-R^2$ | 5 | 5 | 5 | $CH_3-(CH_2)_mC(O)-O-$ | 38 |
| 21 | $CH_3(CH_2)_5CH(OH)-(CH_2)_{10}-C(O)O-$ | H | 20 | 20 | 20 | H | |
| 22 | $CH_3(CH_2)_5CH(OH)-(CH_2)_{10}-C(O)O-$ | $-C(O)-R^2$ | 5 | 5 | 5 | H | |
| 23 | $CH_3(CH_2)_5CH(OH)-(CH_2)_{10}-C(O)O-$ | H | 5 | 10 | 5 | H | |
| 24 | $CH_3-(CH_2)_7-CH=CH-(CH_2)_7-C(O)O-$ | $-C(O)-R^2$ | 10 | 1 | 0 | H | |
| 25 | $CH_3-(CH_2)_7-CH=CH-(CH_2)_7-C(O)O-$ | H | 10 | 2 | 5 | H | | said silicone should have at least 40% by weight polyoxyethylene in the molecule.

Dimethicone Copolyol Examples

Example 1-10

| Example | x | y | d | e | f | z | $R^4$ |
|---|---|---|---|---|---|---|---|
| 1 | 0 | 1 | 0 | 0 | 5 | 1 | 10 |
| 2 | 10 | 2 | 10 | 1 | 10 | 2 | 12 |
| 3 | 20 | 7 | 8 | 20 | 20 | 10 | 12 |
| 4 | 30 | 9 | 20 | 5 | 20 | 20 | 16 |
| 5 | 40 | 11 | 5 | 0 | 0 | 5 | 12 |
| 6 | 50 | 15 | 20 | 20 | 20 | 45 | 10 |
| 7 | 60 | 19 | 15 | 10 | 10 | 5 | 12 |
| 8 | 100 | 25 | 9 | 3 | 15 | 10 | 16 |
| 9 | 150 | 35 | 15 | 0 | 0 | 4 | 18 |
| 10 | 200 | 45 | 10 | 0 | 0 | 1 | 22 |

| | Compositions of the Present Invention | | | |
|---|---|---|---|---|
| | Poloxomer Compound | | Alkyl Dimethicone Copolyol | |
| Example | Example | Grams | Example | Grams |
| 25 | 1 | 95.0 | 11 | 5.0 |
| 27 | 2 | 90.0 | 12 | 10.0 |
| 28 | 3 | 85.0 | 13 | 15.0 |
| 29 | 4 | 80.0 | 14 | 20.0 |
| 30 | 5 | 75.0 | 15 | 25.0 |
| 31 | 6 | 70.0 | 16 | 30.0 |
| 32 | 7 | 65.0 | 17 | 35.0 |
| 33 | 8 | 60.0 | 18 | 40.0 |
| 34 | 9 | 55.0 | 19 | 45.0 |
| 35 | 10 | 50.0 | 20 | 50.0 |
| 36 | 11 | 45.0 | 21 | 55.0 |
| 37 | 12 | 35.0 | 22 | 65.0 |
| 38 | 13 | 25.0 | 23 | 75.0 |
| 39 | 14 | 10.0 | 24 | 85.0 |
| 40 | 15 | 5.0 | 25 | 95.0 |

Application Examples

In order to show the effectiveness of the compositions of the present invention as conditioners on hair and skin the following formula was evaluated;

Shampoo Formula

| Material | % |
|---|---|
| Water | 37.9 |
| Disodium EDTA | 0.1 |
| Sodium Laureth-2-sulfate | 45.0 |
| Cocamidopropyl betaine | 8.0 |
| Cocamid MEA | 3.0 |
| Composition Example | 5.0 |
| NaCl | 1.0 |

The hair conditioning was evaluated using half head salon tests and a scale from 1-5 (with 5 being excellent) was used. The following shows the results:

| Example | Composition Example | Evaluation |
|---|---|---|
| 41 | 35 | 4 |
| 42 | 37 | 4 |
| 43 | 32 | 5 |
| 44 | 38 | 4 |
| 45 | 31 | 4 |

The control was run without added compositions of the present invention. The evaluation produced a rating of 2. For comparison, example 2 of U.S. Pat. No. 5,226,923 to O'Lenick was evaluated. The evaluation produced a rating of 2. The data shows that the compositions of the present invention are effective conditioners when applied to hair.

The compositions of the present invention were found to have outstanding wet comb properties when evaluated against formulations that contain only dimethicone copolyol compounds lacking the critical alkyl group. The alkyl containing compounds were preferred in the area of wet comb by a ration of 10 to 1.

Additionally the compounds of the present invention were diluted in water to a concentration of 10% by weight and evaluated for skin feel by a panel of 20 people. The compositions of the present invention were found to have outstanding skin feel when evaluated against formulations that contain only dimethicone copolyol compounds lacking the critical alkyl group. The alkyl containing compounds were preferred in the area of wet comb by a ration of 8 to 1 by our panel. The compounds with the critical alkyl group lacked a sticky feel and were judged to have an elegant feel on the skin.

This combination of properties make the compounds of the present invention highly desirable in personal care applications.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A composition which comprises;
   (a) from between 5% to 95% by weight of a poloxomer ester conforming to the following structure:

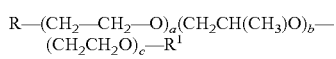

wherein;

R and $R^1$ are selected from the group consisting of H and $—C(O)—R^2$, with the proviso that both R and R1 are not both H;

a and c are each independently integers ranging from 0 to 20, with the proviso that a+c be at least 5;

b is an integer ranging from 1 to 20;

with the proviso that a+c be at least 5;

$R^2$ is selected from the group consisting of;

$CH_3—(CH_2)_m C(O)—O—$;  $CH_3\ (CH_2)_5\ CH(OH)—(CH_2)_{10}—C(O)O—$;

$CH_3—(CH_2)_7—CH=CH—(CH_2)_7—C(O)O—$; and ricionelic;

m is an integer ranging from 6 to 38;

said poloxamer ester has at least 40% by weight polyoxyethylene in the backbone; and (b) between 95% to 5% by weight of a silicone conforming to the following structure;

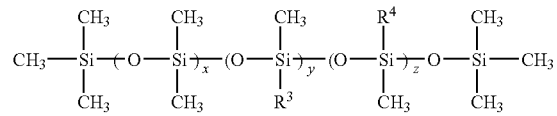

wherein;

$R^3$ is $(CH_2)_3—O—(CH_2CH_2—O)_d(CH_2CH(CH_3)O)_e—(CH_2CH_2O)_f—H$ $R^4$ is alkyl having 10 to 22 carbon atoms;

x is an integer ranging from 0 to 200;

y is an integer ranging from 1 to 45;

z is an integer ranging from 1 to 45:

d is an integer ranging from 0 to 20;

e is an integer ranging from 0 to 20;

f is an integer ranging from 0 to 20;

with the proviso that d+f be at least 5;

said silicone has at least 40% by weight polyoxyethylene in the molecule.

2. A composition of claim 1 wherein $R^1$ is H and R is $—C(O)—R^2$.

3. A composition of claim 1 wherein both R and $R^1$ are $—C(O)—R^2$.

4. A composition of claim 1 wherein $R^2$ is $CH_3—(CH_2)_m C(O)—O—$.

5. A composition of claim 1 wherein $R^2$ is $CH_3(CH_2)_5\ CH(OH)—(CH_2)_{10}—C(O)O—$.

6. A composition of claim 1 wherein $R^2$ is $CH_3—(CH_2)_7—CH=CH—(CH_2)_7—C(O)O—$.

7. A composition of claim 1 wherein e is 0.

8. A composition of claim 1 wherein e is 1 to 5.

9. A composition of claim 1 wherein x is 0.

10. A process of conditioning hair and skin which comprises contacting the hair and skin with an effective conditioning concentration of a composition which comprises;

(a) from between 5% to 95% by weight of a poloxomer ester conforming to the following structure:

$$R-(CH_2CH_2-O)_a(CH_2CH(CH_3)O)_b-(CH_2CH_2O)_c-R^1$$

wherein;

R and $R^1$ are selected from the group consisting of H and $-C(O)-R^2$, with the proviso that both R and $R^1$ are not both H;

a and c are each independently integers ranging from 0 to 20, with the proviso that a+c be at least 5;

b is an integer ranging from 1 to 20;

with the proviso that a+c be at least 5;

$R^2$ is selected from the group consisting of:

$CH_3-(CH_2)_mC(O)-O-$;  $CH_3(CH_2)_5$ $CH(OH)-(CH_2)_{10}-C(O)O-$;

$CH_3-(CH_2)_7-CH=CH-(CH_2)_7-C(O)O-$; and ricionelic;

said poloxomer ester should have at least 40% by weight polyoxyethylene in the backbone; and (b) between 95% to 5% by weight of a silicone conforming to the following structure;

$$CH_3-Si(CH_3)(CH_3)-(O-Si(CH_3)(CH_3))_x-(O-Si(CH_3)(R^3))_y-(O-Si(R^4)(CH_3))_z-O-Si(CH_3)(CH_3)-CH_3$$

wherein;

$R^3$ is $(CH_2)_3O-(CH_2CH_2-O)_d(CH_2CH(CH_3)O)_e-(CH_2CH_2O)_f-H$ $R^4$ is alkyl having 10 to 22 carbon atoms;

x is an integer ranging from 0 to 200;

y is an integer ranging from 1 to 45;

z is an integer ranging hum 1 to 45:

d is an integer ranging from 0 to 20;

e is an integer ranging from 0 to 20;

f is an integer ranging from 0 to 20;

with the proviso that d+f be at least 5;

said silicone has at least 40% by weight polyoxyethylene in the molecule.

11. A process of claim 10 wherein said effective conditioning concentration ranges from between 0.5% and 60% by weight of the composition in water.

12. A process of claim 11 wherein R' is H and R is $-C(O)-R^2$.

13. A composition of claim 11 wherein both R and $R^1$ are $-C(O)-R^2$.

14. A process of claim 11 wherein $R^2$ is $CH_3-(CH_2)_nC(O)-O-$.

15. A process of claim 11 wherein $R^2$ is $CH_3(CH_2)_5 CH(OH)-(CH_2)_{10}-C(O)O-$.

16. A process of claim 11 wherein $R^2$ is $CH_3-(CH_2)_7-CH=CH-(CH_2)_7-C(O)-O-$.

17. A process of claim 11 wherein e is 0.

18. A process of claim 11 wherein e is 1 to 5.

19. A process of claim 10 wherein $R^4$ is alkyl having 12 carbon atoms.

20. A process of claim 10 wherein $R^4$ is alkyl having 16 carbon atoms.

* * * * *